United States Patent [19]
Russell

[11] Patent Number: 4,857,062
[45] Date of Patent: Aug. 15, 1989

[54] CATHETER INTRODUCER VALVE
[75] Inventor: Michael A. Russell, Cohasset, Mass.
[73] Assignee: Medical Parameters, Inc., Woburn, Mass.
[21] Appl. No.: 166,000
[22] Filed: Mar. 9, 1988
[51] Int. Cl.⁴ .............................................. A61M 5/00
[52] U.S. Cl. ................... 604/256; 137/846; 251/149.1; 604/167; 604/905
[58] Field of Search ................. 237/846; 251/149.1; 604/167, 169, 256, 905, 283

[56] References Cited
U.S. PATENT DOCUMENTS

| | | | |
|---|---|---|---|
| 4,161,949 | 7/1979 | Thanawalla | 604/905 X |
| 4,405,163 | 9/1983 | Voges et al. | 285/305 |
| 4,436,519 | 3/1984 | O'Neill | 604/256 X |
| 4,439,188 | 3/1984 | Dennehy et al. | 604/283 |
| 4,452,473 | 6/1984 | Ruschke | 285/81 |
| 4,580,573 | 4/1986 | Quinn | 128/657 |
| 4,610,674 | 9/1986 | Suzuki et al. | 604/282 |
| 4,626,245 | 12/1986 | Weinstein | 604/167 |
| 4,631,056 | 12/1986 | Dye | 604/905 X |
| 4,655,752 | 4/1987 | Honkanen et al. | 604/167 X |

OTHER PUBLICATIONS
*Anesthesiology;* "Introducer Sheath Malfunction Producing Insidious Air Embolism"; Cohen et al.; vol. 67, No. 4, Oct. 1987; pp. 573–575.
Brochure from American Pharmaseal Company; "Pulmonary Artery Catheter Insertion Tray, Kits and Separate Components".

*Primary Examiner*—Dalton L. Truluck
*Attorney, Agent, or Firm*—Hamilton, Brook, Smith & Reynolds

[57] ABSTRACT

The catheter insertion valve of the present invention comprises a central tubular body and a non-removable tubular cap that can be screwed onto the body wherein a bore extending through the body and the cap defines a pathway for a catheter. Such catheters are inserted into arteries, organs or body cavities for the purpose of introducing medications of instruments for treatment, diagnosis or the performing of in vivo procedures. A seal located within the central body of the valve is used to form a fluid-tight seal about the catheter, guidewire or other instrument extending therethrough. Alternatively, the seal can completely close off the pathway when it is not being used for catheter insertion thereby preventing air entrainment. The central body is provided with one or more seal position indicators to indicate to the operator that a seal has been formed about a catheter or guidewire of standard dimension. The seal is manually adjusted by rotating the non-removable cap. The cap is formed on a mold, removed prior to cooling and then reformed by annealing the cap prior to mounting onto the central body of the valve.

12 Claims, 3 Drawing Sheets

CATHETER INTRODUCER VALVE

BACKGROUND

The present invention relates to a valve assembly used for coupling a catheter to a cannula to provide a pathway for introducing the catheter into internal arteries, organs, or cavities.

Such coupling or luer connectors are widely used for controlling the introduction of medications or instruments into the human body. It is imperative in medical applications that a dependable, inexpensive and fluid-tight valve be provided for this purpose.

A prior art device used for providing a fluid-tight pathway for the introduction of catheters is illustrated in FIG. 1.

A central housing 10 normally comprised of plastic, has a port cavity 11 at one end for retaining a four element system for sealing a catheter extending along the pathway 38. A duck bill 32 has a slit at the lower end which opens when the catheter is inserted. The one-way valve or "duck bill" 32 is used to prevent the leakage or flashback of blood or fluid from the inner cavity 44 into the port cavity 11 when the catheter is removed from pathway 38. The slit on the duck bill 32 generally does not form a fluid-tight seal about the catheter. A flexible plastic tube 28 inserted between two washers 26 and 30 is used to form a fluid seal about a catheter guidewire or other intravenous instruments introduced via a cannula.

The seal 28 operates by deforming under pressure applied by screwing a cap 12 with threads 14 onto the housing threads 24 such that the annular surface 42 compresses the seal 28. The inner surface of seal tube 28 deforms against the outer wall of a catheter positioned along path 38 to form a fluid-tight seal.

When the cap 12 is unscrewed from the housing 10, it is retained on the end of the housing by a pair of rings 18 and 22. Ring 18 protrudes outwardly from the inner cylinder 41 that supports the annular compression surface 42. Ring 22 protrudes inwardly from the surface 20 of the housing at the open end of cavity 11. The cap 12 snaps onto the housing 10 by manually pushing ring 18 through the hole defined by ring 22.

The rings 18 and 22 for retaining the cap 12 on the housing have permitted the easy removal of the cap. The application of 3-5 lbs. of pressure to the cap 12 has been sufficient to remove it from the housing 10. As a result, the cap is easily removed and misplaced resulting in the inability to properly seal the pathway 38. This results in the necessity of replacing the valve, or worse, it can endanger the patient if the valve continues to be used.

The failure to form a seal about the catheter or to close the pathway 38 after removal of the catheter can result in the entrainment of air into the blood stream. The intravascular entrainment of air can occur with very minor negative pressures, yet can lead to hypotension and hypoxia within the patient under treatment. If air entrainment is rapid enough, an acute fall in arterial and pulmonary artery pressures can occur.

The cap 12 can also be tightened to the point of causing the collapse of one or more lumens within the catheter and thereby slowing or stopping the flow of fluid therein. As a result, introducer valves which are used frequently during operative and post-operative procedures and which have any undetected blockage within catheter lumens can have deleterious consequences.

The cap 12 has generally been made from a rigid PVC material. The cap is formed on a mold and then cooled before it is removed from the mold to avoid deformation.

SUMMARY OF THE INVENTION

This invention relates to a locking valve assembly and a method of making the same. In particular, the invention relates to a locking valve assembly for sealing about a catheter comprising a first tubular body or housing that is externally threaded and having an inclined circumferential ridge contiguous with the threads and a second tubular body or cap having a proportional opening at a distal end suitable for receiving the first tubular body. The cap has an inner cylindrical bore member through which a catheter can be passed. The cap is partially threaded on an internal surface of an outer cylindrical portion such that the internal threads mate with the threads of the housing. A smooth interior surface of the outer cylindrical portion of the cap extends to the distal end wherein the interior surface protrudes inwardly to form a rim disposed at an angle suitable to retain the circumferential ridge of the housing. The mating of the cap and the housing form a non-removable interlock at the point where the ridge and the rim engage.

In another embodiment, the locking valve assembly has a locking position indicator which is located on the housing such that when the housing and cap are mated, the locking position indicator will mark where a seal is formed about a standard catheter diameter such as a 7-7.5 French catheter. This prevents the over-tightening of the catheter which can result in the occlusion of catheter lumens while insuring that the catheter cannot be moved.

In still another embodiment, the locking valve assembly has a two element seal within the housing such that when the cap is sufficiently tightened, the two elements form a seal to prevent fluid leakage about a catheter. The seal operates to lock the catheter into a desired position thereby preventing movement during catheter operation. Alternatively, when the catheter is removed, the cap can be tightened to form a seal thereby preventing air from passing through the pathway along which the catheter normally extends.

In still another embodiment, the locking valve assembly has a tubular appendage extending perpendicularly from the first tubular body suitable for engaging an 8.5 French inner diameter flexible tube. This provides for a much greater flow of fluid through the valve assembly than previously permitted.

The above and other features of the invention including various novel details of construction and combinations of parts will now be more particularly described with reference to the accompanying drawings and pointed out in the claims. It will be understood that the particular catheter introducer valve embodying the invention is shown by way of illustration only and not as a limitation of the invention. The principles and features of this invention may be employed in varied and numerous embodiments without departing from the scope of the invention.

DETAILED DESCRIPTION OF THE INVENTION

Figure 2:
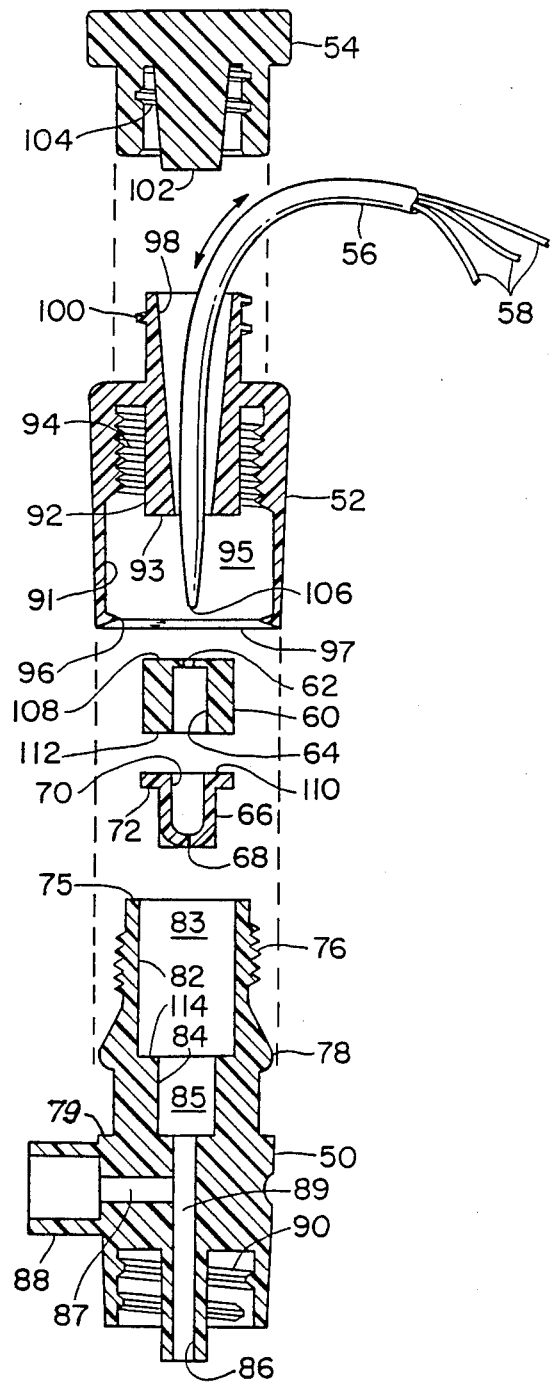
FIG. 2 is an exploded cross-sectional view of a preferred embodiment of the present invention.

A preferred embodiment of the locking valve assembly of the present invention is illustrated in FIG. 2.

Figure 1:
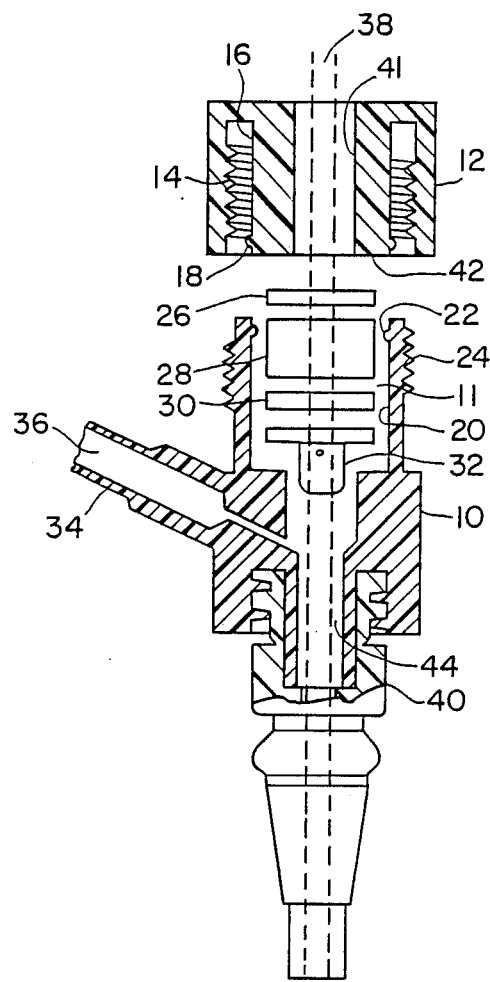
FIG. 1 is a prior art introducer sheath assembly.

Catheters are normally introduced into the human body by first inserting a needle into the desired artery. A guidewire is then inserted through the needle and the needle is removed. A dilator is then inserted through the valve assembly and a sheath attached to the distal end of the valve. The dilator is then directed by the guidewire into the desired position and both the guidewire and the dilator are removed. A catheter is then inserted through the valve and attached the sheath into the desired position. A heparin based solution has been introduced through the side port 36 of FIG. 1 to prevent clotting at the base of the sheath and about the catheter. This has required a relatively low fluid flow rate as compared with the present need to infuse large amounts of fluid through the side port.

A housing 50 is constructed to mate with a cap 52 such that the proximal or open end 75 of the housing 50 is inserted into a cavity 95 of the cap 52. The threading 76 of the housing 50 mates with the threading 94 of the cap 52 upon insertion. An inner wall 91 of the cap surrounds the cavity 95 within the cap. An open end 97 of the cap 52 has an inwardly extending rim 96. The ring 96 is defined so as to snugly engage a peripheral ridge 78 that protrudes from the outer wall of the housing 50.

The cap 52 and housing 50 are formed to within specific dimensional tolerances. As a result, the cap 52 requires a substantial amount of mechanical pressure to be mounted onto the housing 50 such that the rim 96 can be forced over the ridge 78. Once mounted, the cap 52 cannot be manually removed from the housing. A preferred embodiment of the present invention utilizes plastic materials that require at least 30 lbs. of pressure to be exerted to remove the cap 52 from the housing 50. The cap 52 cannot be removed without causing permanent damage to the cap.

When the catheter is removed, the cap 52 is screwed completely clockwise so that the distal end 97 of cap 52 is against surface 79 of housing 50. A sealing cap 54 with threading 104 can be screwed onto the threading 100 of cap 52 to provide a fluid-tight seal along surface 98 to maintain the sterility of the seal area. A lower portion of the housing 50 has internal threads 90 to provide for the connecting of the valve to the cannula which guides the entry of the catheter into the cavity.

The wall 86 of the pathway at the lower end of the housing 50 has a port 87, having an inner diameter of 8.5 French, providing for the transmission of fluids directly into the catheter pathway without the necessity of transporting the fluid through the sealing portion of the valve. A tubular section 88 extends orthogonally from the port 87 and operates to receive a large gauge tube used to introduce fluids through the port 87 and tube 88 fixture provides for the use of 8.5 inner diameter French tubing. The use of this large tubing permits the transmission of 2 to 3 times the quantity of fluid than prior art connectors having side port structures.

Figure 3:
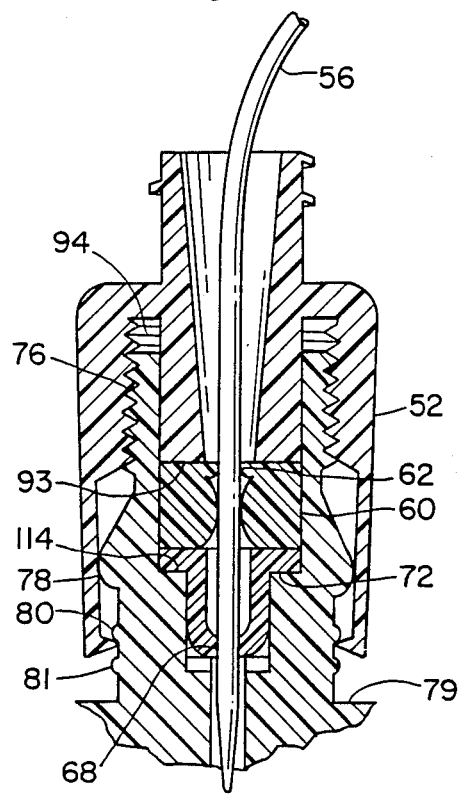
FIG. 3 is a magnified cross-sectional view of the non-removable cap and a lock position indicator.

When the cap 52 is screwed onto the housing 50, a means for sealing located within the cavity 83 of the housing compresses to form a fluid-tight seal about the catheter 56. The sealing of the catheter 56 is shown in more detail in FIG. 3. The means for sealing the catheter pathway extending through the cap 52 and the housing 50 in a preferred embodiment of the invention utilizes a first element 66, often referred to as a "duck bill," and a second flexible element 60 that is compressed to form a fluid-tight seal about the catheter 56.

The first element or duck bill 66 has a peripherally extending flange having an annular surface 72 that contacts the surface 114 of the housing. The lower portion of the first element 66 is placed within the inner cavity 85 of the housing 50. A slit 68 located within the lower portion of element 66 opens to receive the catheter 56. The slit 68 will reseal upon removal of the catheter to prevent fluids located in the catheter pathway 89 from leaking into the upper housing cavity 83. The slit 68 will not prevent the transmission of air from outside the valve into the cavity 89 when the catheter is removed from the valve if a threshold negative pressure within the cavity 89 is exceeded. The re-sealing performance of the slit can degrade after repeated use. Valves or luer connectors of the prior art have used obdurators which are inserted into the catheter pathway to seal the pathway when not in use.

The second flexible element 60 is directed towards the prevention of the leakage of air into the cavity 89, and also therefore, preventing the introduction of air into blood carrying arteries or cavities into which the catheter is inserted. The upper portion of the element 60 has a small diameter tube 62 which communicate with a larger diameter portion with inner wall 64. The element 60 is formed as a one-piece mold and is preferably comprised of silicone.

Figure 4:
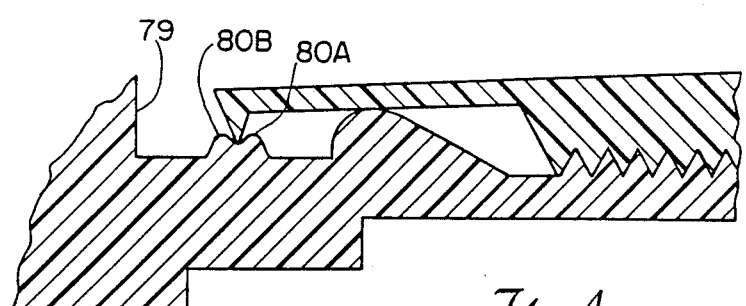
FIG. 4 is a magnified cross sectional view of another preferred embodiment of the invention.

The preferred embodiment of the cap 52 of the present invention has been made using a nylon material rather than the rigid PVC of prior art connectors. The cap is formed on a mold such that the rim 96 has a wedge shaped cross-section extending over an approximately 40° arc. Each side of the inwardly directed wedge-shaped rim 96 is therefore at a 20° angle from a normal extending from the interior surface 91 in FIG. 2. This structure provides for ease of mounting and use of the indicators 80 and 81 of FIG. 3, and indicator 80A and B, of FIG. 4.

The molding process comprises the formation of the cap 52 on a pin. The cap 52 is removed from the pin before it is permitted to cool. The rim 96 deforms when the cap 52 is removed. The cap is then permitted to cool and is then placed in an oven to anneal the cap so that the rim 96 resumes the shape it had prior to removal from the pin. Annealing the cap at 200° F. for 8 hours has proven sufficient to yield a cap having the structure necessary to prevent manual removal of the cap 52 from the valve housing 50 while in normal use.

I claim:

1. A locking valve assembly for sealing about a catheter comprising:
    a first tubular body for housing a seal wherein said body has a circumferential ridge in a peripheral surface of the body and is externally threaded at a proximal end such that the threads are positioned between the end and the ridge; and
    a second tubular body having a proportioned diameter at a distal end to receive the proximal end of said first tubular body, said second tubular body having a bore member forming a tubular pathway with said first body and being partially threaded on an internal surface such that said internal threads can mate with the threads of said first tubular body and wherein the internal surface extends to the distal end where said surface protrudes inwardly to form a rim that extends over and retains said ridge of the first tubular body such that said first tubular body cannot be manually removed from the second tubular body.

2. The locking valve assembly of claim 1 further comprising a flexible sealing element such that when the second body is screwed onto the first body along the threads, the bore member compresses the sealing element.

3. The locking valve assembly of claim 2 wherein said seal compresses to form a fluid tight seal about a catheter extending along said tubular pathway.

4. The locking valve assembly of claim 2 wherein said seal compresses to form a fluid tight seal along said tubular pathway.

5. The locking valve assembly of claim 1 further comprising a threaded sealing cap that can be screwed onto an externally threaded proximal end of said second tubular body to form a fluid tight seal across the tubular pathway.

6. A locking valve assembly for sealing about a catheter having a sealing position indicator comprising:
 a first tubular body comprising an externally threaded portion at one end, a circumferential ridge contiguous with said threaded portion, and a peripheral ledge parallel to the ridge and positioned to one side of the ridge opposite the threaded portion;
 a second tubular body having a proportioned diameter at a distal end to receive said first tubular body, said second tubular body having a bore member forming a tubular pathway with said first body and being partially threaded internally such that said internal threads can mate with threads of said first tubular body and having an interior surface extending to the distal end wherein said tubular body portrudes inwardly to form a rim suitable to retain said ridge of first tubular body such that the mating of said first and second tubular bodies form an interlock where said rim and ridge are engaged; and
 a flexible diaphragm seal positioned within the first tubular body and having an opening through which the catheter extends such that the threading of the first and second tubular bodies together compresses the diaphragm to form a seal wherein the passage of the rim over the ledge indicates the sealing of the catheter within the pathway.

7. The locking valve assembly of claim 6 further comprising a plurality of locking position indicators to indicate the locking of the catheter pathway at a plurality of predetermined diameters, thereby preventing unwanted occlusion of lumens within the catheter.

8. A locking valve assembly comprising:
 a first tubular body housing a first sealing element and a second sealing element, said first body being externally threaded at one end and having a circumferential ridge positioned further from the end than said threads; and
 a second tubular body having a proportioned diameter to receive said first tubular body, said second tubular body having a bore member forming a tubular pathway with the first body and being partially threaded internally such that said internal threads mate with threads of said first tubular body and having an inwardly directed rim that engages the ridge, thereby securing the first and second bodies;
 said first element being a self-sealing flexible diaphragm housed within said first tubular body for substantially preventing the flow of fluids from the first body into the bore; and
 said second element being made of resiliently deformable material adjacent the first element and such that the compression of the second element upon sufficient threading of the second body onto the first body deforms to seal the pathway.

9. The locking valve assembly of claim 8 wherein said second element further comprises a tube having a large inner diameter at one side and a small inner diameter at the opposite side abutting said first element.

10. The locking valve assembly of claim 8 wherein said second element is adhesively secured to said first element.

11. The locking valve assembly of claim 8 wherein said second element is comprised of silicone.

12. The locking valve assembly of claim 8 wherein said first element is comprised of silicone.

* * * * *